(12) United States Patent
Wang et al.

(10) Patent No.: US 11,471,144 B2
(45) Date of Patent: Oct. 18, 2022

(54) VERTEBRAL END PLATE PROCESSING DEVICE

(71) Applicant: Zhirong Wang, Jiangsu (CN)

(72) Inventors: Zhirong Wang, Zhangjiagang (CN); Ke Ji, Zhangjiagang (CN); Wei Miao, Zhangjiagang (CN); Danyong Li, Zhangjiagang (CN); Cheng Feng, Zhangjiagang (CN)

(73) Assignee: ZHIRONG WANG, Jiangsu (CN)

( * ) Notice: Subject to any disclaimer, the term of this patent is extended or adjusted under 35 U.S.C. 154(b) by 201 days.

(21) Appl. No.: 16/982,973

(22) PCT Filed: Aug. 24, 2018

(86) PCT No.: PCT/CN2018/102172
§ 371 (c)(1),
(2) Date: Sep. 21, 2020

(87) PCT Pub. No.: WO2019/242091
PCT Pub. Date: Dec. 26, 2019

(65) Prior Publication Data
US 2021/0030407 A1      Feb. 4, 2021

(30) Foreign Application Priority Data

Jun. 22, 2018 (CN) .......................... 201810654786.7

(51) Int. Cl.
*A61B 17/16* (2006.01)
*A61B 17/02* (2006.01)
*A61B 90/00* (2016.01)

(52) U.S. Cl.
CPC ........ *A61B 17/025* (2013.01); *A61B 17/1671* (2013.01); *A61B 90/06* (2016.02); *A61B 2017/0256* (2013.01); *A61B 2090/065* (2016.02)

(58) Field of Classification Search
CPC .......... A61B 17/025; A61B 2017/0256; A61B 17/1671; A61B 17/1659
See application file for complete search history.

(56) References Cited

U.S. PATENT DOCUMENTS

2008/0177259 A1      7/2008   Wu
2015/0282797 A1 *   10/2015   O'Neil ................. A61B 8/0875
                                                                 606/279

FOREIGN PATENT DOCUMENTS

CN          1748654 A      3/2006
CN        102846352 A      1/2013
(Continued)

OTHER PUBLICATIONS

International Search Report and Translation, National Intellectual Property AdminisliaLion, PRC (ISA/CN), PCT/CN2018/102172, dated Mar. 11, 2019, 11 pages.

*Primary Examiner* — Samuel S Hanna
(74) *Attorney, Agent, or Firm* — Faegre Drinker Biddle & Reath LLP (57) ABSTRACT

A vertebral end plate processing device includes a handle, a vertical opening mechanism, a horizontal expansion mechanism and a processing mechanism. When the processing device is in a non-working state, the vertical opening mechanism and the horizontal expansion mechanism maintain a contracted state, and a processing portion is located within a vertical space between opening members. When the processing device is in a working state, the opening members of the vertical opening mechanism are in contact with a bone surface of a vertebral body and vertically open same. An arc-shaped expansion block of the horizontal expansion mechanism drives a conveying member for horizontal expansion so that the processing portion is horizontally removed from the vertical space of the opening members (Continued)

and is in contact with the bone surface of the vertebral body. A control portion controls the conveying member to move.

10 Claims, 6 Drawing Sheets

(56) References Cited

FOREIGN PATENT DOCUMENTS

| | | | |
|---|---|---|---|
| CN | 104815388 | A | 8/2015 |
| CN | 106163455 | A | 11/2016 |
| CN | 106963522 | A | 7/2017 |
| WO | 2008042155 | A1 | 4/2008 |

* cited by examiner

VERTEBRAL END PLATE PROCESSING DEVICE

The present application is the national phase of international application No. PCT/CN2018/102172, titled "VERTEBRAL END PLATE PROCESSING DEVICE", filed on Aug. 24, 2018, which claims the priority to Chinese Patent Application No. 201810654786.7, titled "VERTEBRAL END PLATE PROCESSING DEVICE", filed with the China National Intellectual Property Administration on Jun. 22, 2018, both of which are incorporated herein by reference.

FIELD

The present application relates to the technical field of medical surgery instruments, and in particular to a vertebral body endplate processing device.

BACKGROUND

Herniated disk of human body is generally caused by carrying heavy objects or due to improper exertion, long-term incorrect posture, great impact on the lower back and other factors. A mild patient may have symptoms of expanded but complete annulus fibrosus, which is clinically referred to as disk bulge, and a severer patient may have symptoms of rupture of the annulus fibrosus, overflow of the vertebral nucleus, and oppression on the spinal nerve, which is clinically referred to as disk herniation or extrusion. In particular, the intervertebral disks of the elderly are more likely to degenerate and malfunction, which may need surgery.

At present, spinal fusion is one of the most commonly used surgical methods in clinical practice, and is an effective method to treat spinal diseases such as spinal tuberculosis, infection, deformity, degenerative disease and disk injury. In the process of intervertebral bone graft fusion, nucleus pulposus forceps, endplate reamers and scrapers need be used to thoroughly remove the nucleus pulposus, annulus fibrosus, cartilage endplate and other tissues in the bone graft intervertebral space, so as to expose the vertebral body bony endplate, increase a bony contact area of the bone graft surface, and make the bone graft surface have enough biological mechanical strength, and then graft the intervertebral fusion cage filled with broken bones, thereby achieving the bone graft fusion.

However, the conventional expansion instruments only function to expand the intervertebral space, and the subsequent endplate processing needs more surgical instruments, has cumbersome steps, consumes more operation time and increases the operation risk. Moreover, during the processing of the vertebral body endplate, the space between different vertebral bodies is different, and even in the same intervertebral space, the height between the upper and lower bony endplates is not consistent. As the endplate is processed, the intervertebral space will be loosened and increased in the process, the expansion instrument needs to be adjusted in time, which affects the subsequent processing operation of the vertebral body endplate to a certain extent.

In view of the above-mentioned problems, it is necessary to provide a processing device that can not only achieve the effect of expanding the vertebral space, but can also synchronously carry out endplate processing operations.

SUMMARY

In view of this, an object of the present application is to provide a vertebral body endplate processing device. The processing device integrates the expansion function and the processing function, which can not only achieve the effect of expanding the intervertebral space, but also can synchronously carry out the endplate processing operations, and is suitable for a case that the height between the bony endplates in the same intervertebral space is irregular, and has a simple structure and is easy to operate.

To achieve the above object, the technical solution of the present application is as follows.

A vertebral body endplate processing device includes a handle, a vertical opening mechanism, a horizontal expansion mechanism and a processing mechanism. Two ends of the handle respectively are a processing end and a control end. The vertical opening mechanism includes a pair of opening members that are symmetrically arranged up and down and arranged at the processing end of the handle. The horizontal expansion mechanism includes a pair of arc-shaped expansion blocks arranged horizontally and a transmission member in contact with an outer side surface of the arc-shaped expansion block. The processing mechanism includes a processing portion vertically arranged on the transmission member and a control portion connected with the transmission member. The arc-shaped expansion block and the processing portion are arranged at the processing end of the handle, and the control portion is arranged at the control end of the handle.

When the processing device is in a non-working state, the vertical opening mechanism and the horizontal expansion mechanism maintain a contracted state, and the processing portion is located within a vertical space between the opening members. When the processing device is in a working state, the opening members of the vertical opening mechanism are in contact with a bone surface of the vertebral body and are vertically opened. The arc-shaped expansion block of the horizontal expansion mechanism drives the transmission member to horizontally expand, so that the processing portion horizontally moves out from the vertical space of the opening members and is in contact with the bone surface of the vertebral body, and the control portion controls the transmission member to move, thereby driving the processing portion to process the bone surface of the vertebral body.

Preferably, the vertical opening mechanism further includes a moving mandrel provided inside the handle and configured to move along an axial direction of the handle. An end of the moving mandrel is connected with the opening members vertically arranged and located at the processing end of the handle. A lifting component configured to cause the opening members to move up and down is provided at the processing end of the handle. The moving mandrel drives the opening members to move and cooperates with the lifting component to vertically broaden the opening members to the same height as the handle.

Preferably, the opening member includes an opening plate with a pressure sensor on the surface. An opening support rod extends at an end portion of the opening plate. A fixing hole is provided on the surface of the opening support rod. An end of the moving mandrel is of a T-shaped structure and penetrates through the fixing hole on the surface of the opening support rod and is fixed, and the other end of the moving mandrel is connected with a handheld control component. A long strip-shaped through hole is provided in a handle body at the control end of the handle. The handheld control component is arranged in the long strip-shaped through hole and is in interference fit with two side walls of the long strip-shaped through hole. The handheld control component moves in the strip-shaped through hole and drives the moving mandrel to move inside the handle.

Preferably, multiple lifting blocks with a tilted lifting surface vertically extend downward on a side of the opening support rod. An accommodating cavity for accommodating the opening support rod is provided at the handle body of the processing end of the handle. A lifting matching block corresponding to the lifting block of the opening support rod is provided in the accommodating cavity. The lifting matching block is provided with a tilted lifting matching surface corresponding to the lifting surface of the lifting block. The opening support rod, the lifting block and the lifting matching block arranged in the accommodating cavity of the handle form the lifting component. The moving mandrel drives the opening support rod to move, and the lifting block on the side of the opening support rod cooperates with the lifting matching block in the accommodating cavity through the contact between the tilted lifting surface and the lifting matching surface, so that the opening support rod moves up and down to drive the opening plates to vertically open, thereby completing the vertical opening operation of the processing device.

Preferably, the horizontal expansion mechanism further includes a handheld rotating member, a connector and a moving rod. The moving rod is connected to block bodies of the arc-shaped expansion blocks through multiple connecting rods. The handheld rotating member is sleeved on the handle body at the control end of the handle and is screwed with the handle body. The connector is fixed in the handheld rotating member, and the handheld rotating member is connected with the moving rod through this connector. The handheld rotating member rotates and moves on the handle body of the handle, thereby driving the moving rod to move along the axial direction of the handle through the connector. The moving rod moves and horizontally pushes the arc-shaped expansion blocks to expand through the connecting rod. Therefore, the transmission member is horizontally expanded, so that the processing portion horizontally moves out from the vertical space of the opening members and contacts with the bone surface of the vertebral body, thereby completing the horizontal expansion operation of the processing device.

Preferably, a pair of fixing accessories arranged symmetrically up and down extend horizontally at the processing end of the handle, the fixing accessories are located in the vertical space of the expansion members, and are provided with through holes. End portions of the pair of arc-shaped expansion blocks are connected with the through holes of the fixing accessories through a pin shaft and serve as horizontal expansion support ends, and cooperate with the moving rod and the connecting rod to realize the horizontal expansion of the arc-shaped expansion blocks.

Preferably, the transmission member is a transmission chain, the transmission chain is in contact with the arc-shaped outer surface of the arc-shaped expansion block, and a first chain wheel engaged with the transmission chain is coaxially provided at the horizontal expansion support end.

Preferably, the processing portion includes multiple processing units. Each of the processing units includes a sleeve and processing knifes symmetrically arranged at two ends of the sleeve. The sleeve is vertically embedded and fixed to the transmission chain. A moving space is provided in the sleeve. A knife head of the processing knife protrudes from the sleeve, and a knife handle of the processing knife is provided in the moving space of the sleeve. An elastic member is connected between the processing knifes.

When the processing device is in the non-working state, the vertical opening mechanism maintains the contracted state. The opening member acts on the knife head of the processing knife, so that the elastic member is compressed under force. The knife handle of the processing knife moves along the axial direction of the sleeve in the moving space of the sleeve, so that the processing portion is accommodated in the vertical space of the opening members. When the processing device is in the working state, the processing portion horizontally moves out from the vertical space of the opening members. The knife handle of the processing knife moves along the axial direction of the sleeve in the moving space under the elastic force of the elastic member until the knife head of the processing knife contacts with the bone surface of the vertebral body.

Preferably, the control portion includes a movement control block and a manual chain wheel. A handle connector and a chain wheel connector extend horizontally on two sides of the movement control block, respectively. The handle connector is movably connected with the control end of the handle by means of insertion. The chain wheel connector is pivotally connected to an axis of the manual chain wheel. The transmission chain is connected to the first chain wheel and the manual chain wheel, and a transmission space for the transmission chain is provided in the handle and the movement control block.

When the processing device is in the working state, the arc-shaped expansion blocks of the horizontal expansion mechanism drive the transmission chain to expand, and the transmission chain is engaged with the manual chain wheel, so that the movement control block and the manual chain wheel move along the axial direction of the handle towards the processing end of the handle. The manual chain wheel is operated to rotate the transmission chain, so that multiple processing units contact with the bone surface of the vertebral body, thereby completing the processing operation of the processing device on the bone surface of the vertebral body.

Preferably, tilted guiding structures are provided at two ends of the transmission space of the transmission chain where the handle and the movement control block are located.

Compared with the conventional technology, the vertebral body endplate processing device provided according to the present application is inserted between two vertebral bodies, the two vertebral bodies are broadened into a suitable gap through the vertical opening mechanism, and then the horizontal expansion mechanism is operated to push out the arc-shaped expansion blocks to expand, so that the processing portion horizontally moves in the vertical space in the vertical opening mechanism and maintains contact with the bone surface of the vertebral body under the action of the elastic force, and at last the manual chain wheel is manually operated. The transmission chain is driven to move by the operation of the manual chain wheel, thereby driving the multiple processing units of the processing portion to process the bone surface of the vertebral body until the whole processing process is completed. The processing device has a simple structure and is easy to operate, can adjust the expansion height, the bone surface processing circuit, and the processing rhythm in real time, and has good clinical popularization.

BRIEF DESCRIPTION OF THE DRAWINGS

To illustrate technical solutions according to the embodiments of the present application or in the conventional technology more clearly, the drawings to be used in the description of the conventional technology or the embodiments are described briefly hereinafter. Apparently, the drawings described hereinafter are only some embodiments of the present application, and other drawings may be obtained by those skilled in the art based on those drawings without creative effort.

Reference numerals and components involved in the drawings are listed as follows:

| | |
|---|---|
| 1 handle; | 2 arc-shaped expansion block; |
| 3 processing portion; | 4 control portion; |
| 5 moving mandrel; | 6 opening plate; |
| 7 opening support rod; | 8 fixing hole; |
| 9 handheld control component; | 10 long strip-shaped through hole; |
| 11 lifting surface; | 12 lifting block; |
| 13 accommodating cavity; | 14 lifting matching block; |
| 15 lifting matching surface; | 16 handheld rotating member; |
| 17 connecting rod; | 18 moving rod; |
| 19 connecting rod; | 20 fixing accessory; |
| 21 through hole; | 22 transmission chain; |
| 23 first chain wheel; | 24 sleeve; |
| 25 moving space; | 26 processing knife; |
| 27 elastic member; | 28 movement control block; |
| 29 manual chain wheel; | 30 handle connector; |
| 31 chain wheel connector; | 32 guiding structure. |

DETAILED DESCRIPTION OF THE EMBODIMENTS

Technical solutions of the present application are described clearly and completely with reference to embodiments hereinafter. Apparently, the described embodiments are only a few rather than all of the embodiments of the present application. Other embodiments obtained by the person skilled in the art without any creative efforts based on the embodiments of the present application fall into the scope of protection of the present application.

Figure 1:
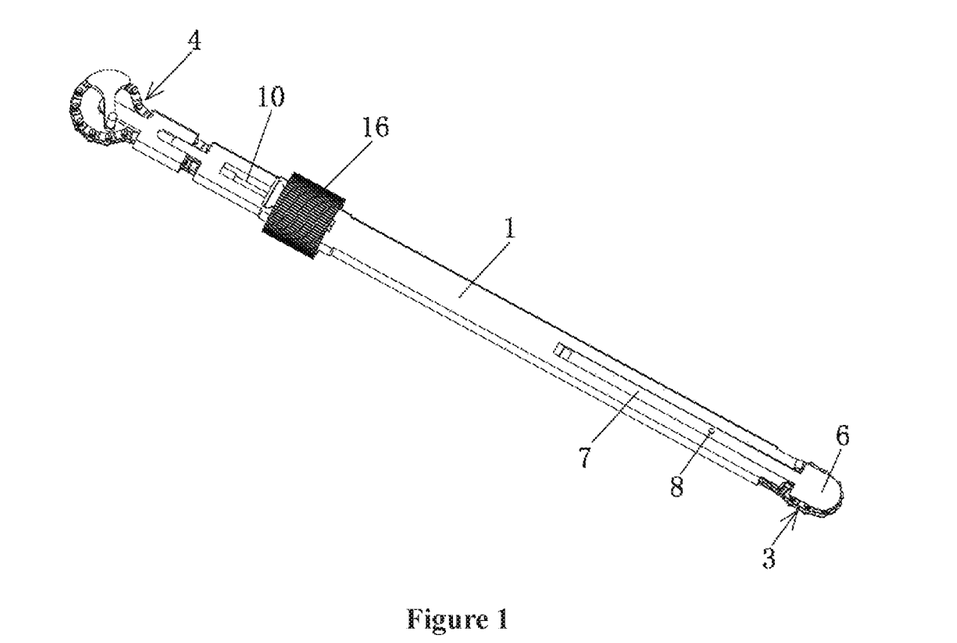
FIG. 1 is a schematic perspective view of a vertebral body endplate processing device according to the present application in a non-working state.
Figure 8:
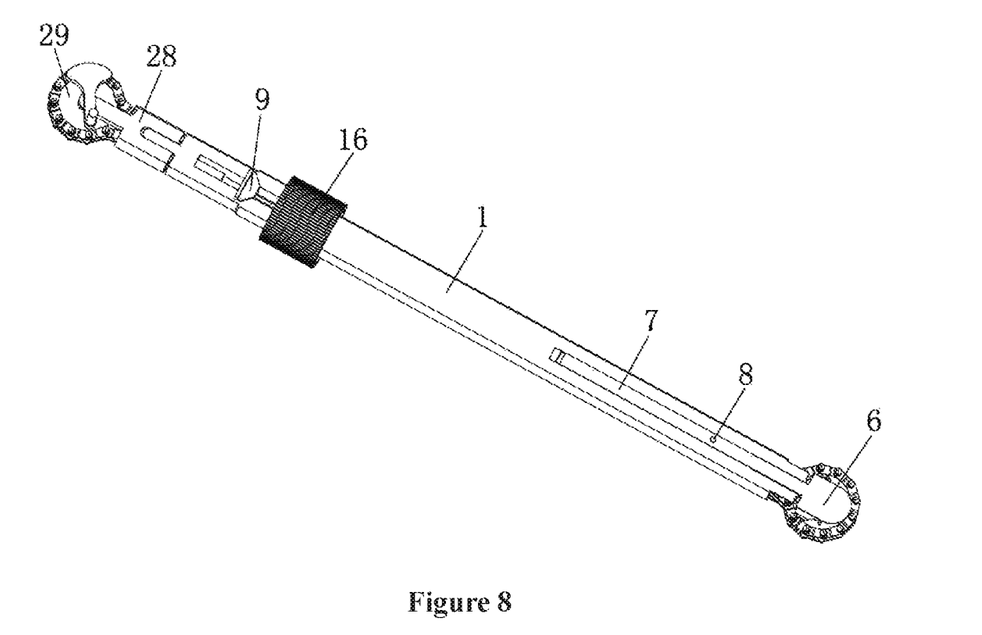
FIG. 8 is a schematic perspective view of the vertebral body endplate processing device according to the present application in a working state.

Referring to FIGS. 1 and 8, a vertebral body endplate processing device includes a handle 1, a vertical opening mechanism, a horizontal expansion mechanism and a processing mechanism. Two ends of the handle 1 respectively are a processing end and a control end. The vertical opening mechanism includes a pair of opening members that are symmetrically arranged up and down and arranged at the processing end of the handle 1. The horizontal expansion mechanism includes a pair of arc-shaped expansion blocks 2 arranged horizontally and a transmission member in contact with an outer side surface of the arc-shaped expansion block 2. The processing mechanism includes a processing portion 3 vertically arranged on the transmission member and a control portion 4 connected with the transmission member. The arc-shaped expansion block 2 and the processing portion 3 are arranged at the processing end of the handle 1, and the control portion 4 is arranged at the control end of the handle 1.

Figure 2:
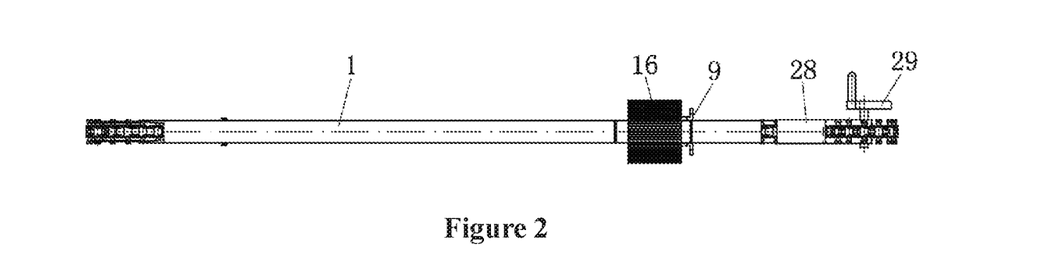
FIG. 2 is a front view of the vertebral body endplate processing device according to the present application in the non-working state.
Figure 3:
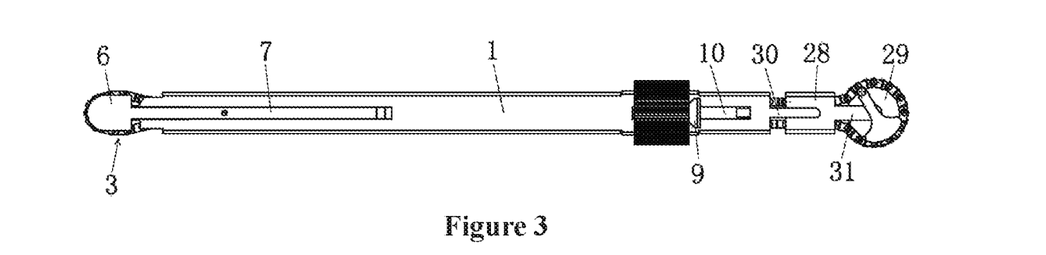
FIG. 3 is a top view of the vertebral body endplate processing device according to the present application in the non-working state.
Figure 9:
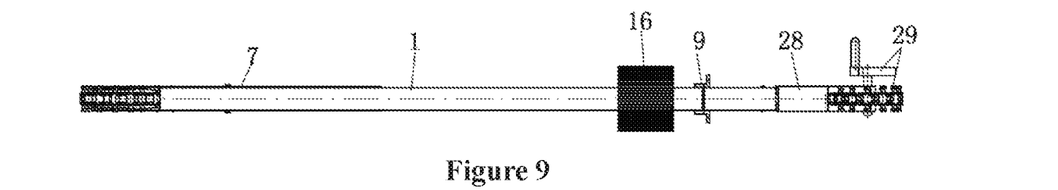
FIG. 9 is a front view of the vertebral body endplate processing device according to the present application in the working state.
Figure 10:
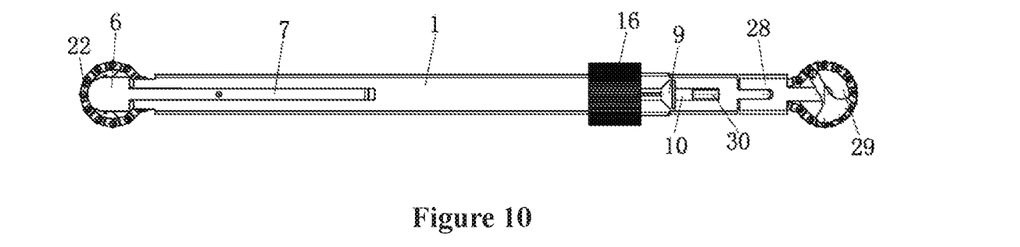
FIG. 10 is a top view of the vertebral body endplate processing device according to the present application in the working state.

When the processing device is in a non-working state, the vertical opening mechanism and the horizontal expansion mechanism maintain a contracted state, and the processing portion 3 is located within a vertical space between the opening members, as shown in FIGS. 1 to 3. When the processing device is in a working state, the opening members of the vertical opening mechanism are in contact with a bone surface of the vertebral body and are vertically opened. The arc-shaped expansion block 2 of the horizontal expansion mechanism drives the transmission member to horizontally expand, so that the processing portion 3 horizontally moves out from the vertical space of the opening members and is in contact with the bone surface of the vertebral body, and the control portion 4 controls the transmission member to move, thereby driving the processing portion 3 to process the bone surface of the vertebral body, as shown in FIGS. 8 to 10.

Figure 4:
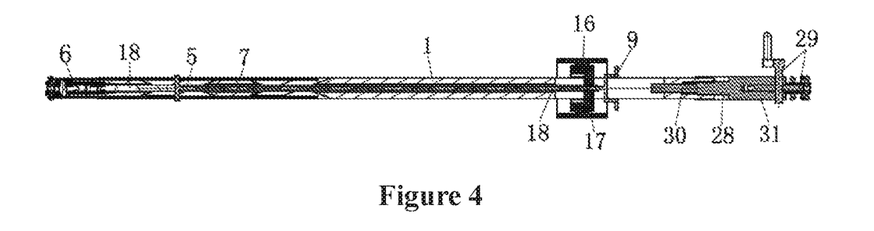
FIG. 4 is a schematic sectional view of FIG. 2.
Figure 11:
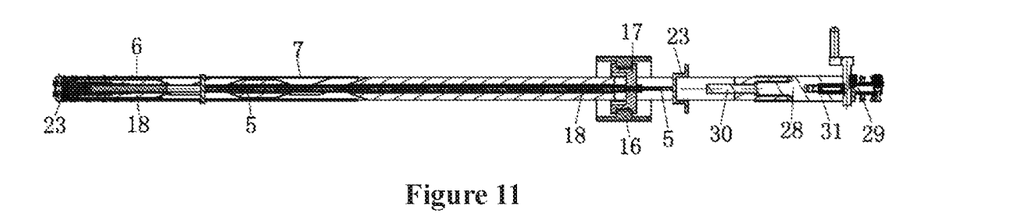
FIG. 11 is a schematic sectional view of FIG. 9.

Referring to FIGS. 4 and 11, the vertical opening mechanism further includes a moving mandrel 5 provided inside the handle 1 and configured to move along an axial direction of the handle 1. An end of the moving mandrel 5 is connected with the opening members vertically arranged and located at the processing end of the handle 1. A lifting component configured to cause the opening members to move up and down is provided at the processing end of the handle 1. The moving mandrel 5 drives the opening members to move and cooperates with the lifting component to vertically broaden the opening members to the same height as the handle.

The opening member includes an opening plate 6 with a pressure sensor (not shown in the figure) on the surface, which can feedback the force from the opening plate 6 of opening the bone surface of the vertebral body in real time. An opening support rod 7 extends at an end portion of the opening plate 6. A fixing hole 8 is provided on the surface of the opening support rod 7. An end of the moving mandrel is 5 of a T-shaped structure and penetrates through the fixing hole 8 on the surface of the opening support rod 7 and is fixed, and the other end of the moving mandrel 5 is connected with a handheld control component 9. A long strip-shaped through hole 10 is provided in a handle body at the control end of the handle 1. The handheld control component 9 is arranged in the long strip-shaped through hole 10 and is in interference fit with two side walls of the long strip-shaped through hole 10. The handheld control component 9 moves in the strip-shaped through hole 10 and drives the moving mandrel 5 to move inside the handle 1. Besides, in order to adjust the intervertebral space in real time, a scale is carved at a side wall of the long strip-shaped through hole 10. The vertical opening height of the processing device can be adjusted according to the scale when the handheld control component 9 is moved, so as to prevent the bone surface of the vertebral body from being damaged by abrupt change of the opening height.

Figure 6:
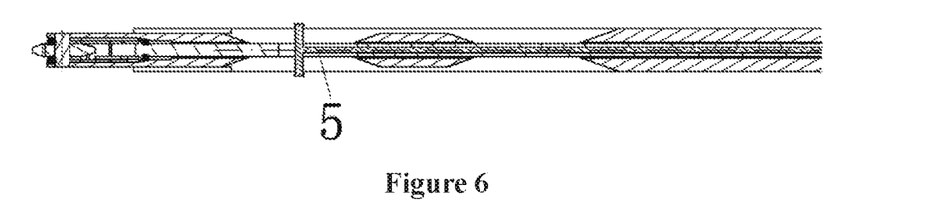
FIG. 6 is a schematic structural view of a portion of a vertical opening mechanism in FIG. 4 located at a processing end of a handle.
Figure 13:
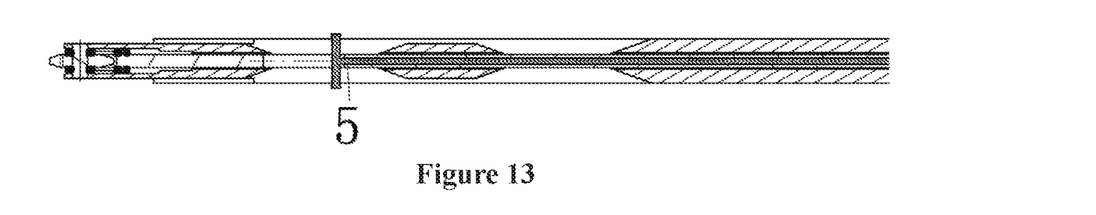
FIG. 13 is a schematic structural view of the portion of the vertical opening mechanism in FIG. 9 located at the processing end of the handle.
Figure 15:
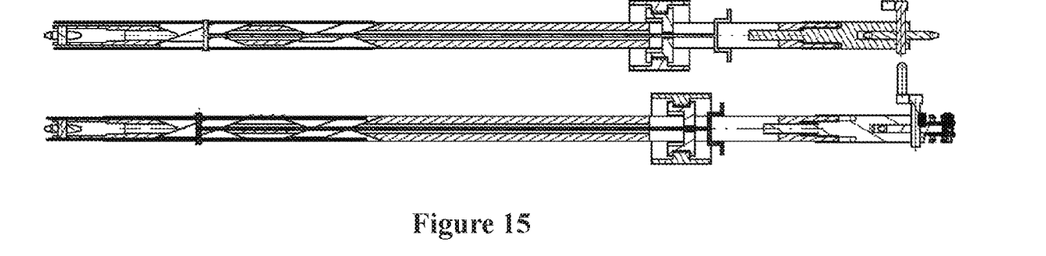
FIG. 15 is a comparison view of the vertical opening mechanism in the working state and the non-working state.
Figure 16:
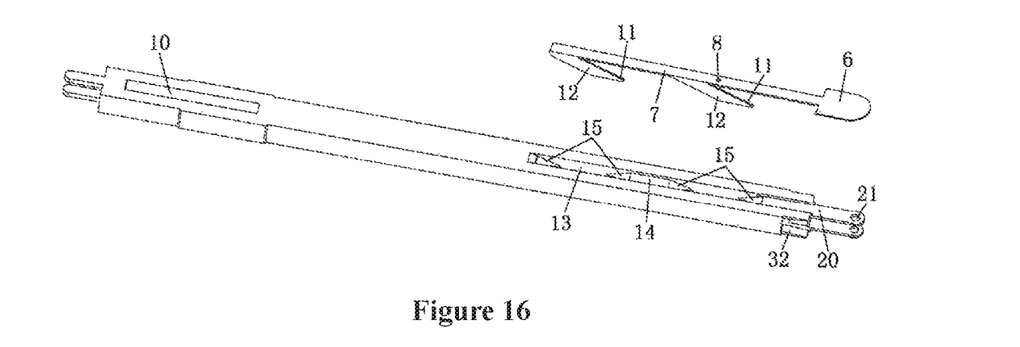
FIG. 16 is a schematic structural view of the handle and an opening member.
Figure 17:
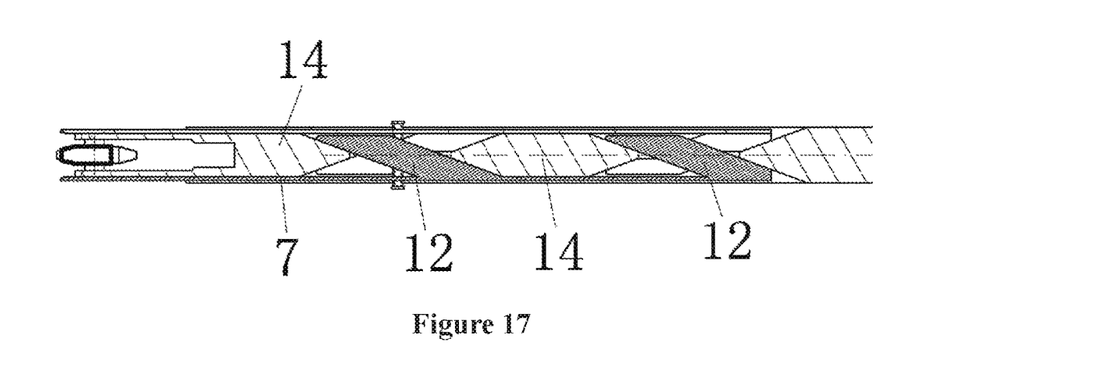
FIG. 17 is a schematic structural view of an assembly of the handle and the opening member.

As the internal space of the handle 1 is limited, a large lifting component cannot be provided. The processing device hereby arranges the lifting components on the opening member and the handle 1 respectively. The two lifting components cooperate with each other. On the one hand, the size of the component is reduced, and on the other hand, the structural reliability of the component can be improved. Referring to FIGS. 16 and 17 for the specific structure, multiple lifting blocks 12 with a tilted lifting surface 11 vertically extend downward on a side of the opening support rod 7. An accommodating cavity 13 for accommodating the opening support rod 7 is provided at the handle body of the processing end of the handle 1. A lifting matching block 14 corresponding to the lifting block 12 of the opening support rod 7 is provided in the accommodating cavity 13. The lifting matching block 14 is provided with a tilted lifting matching surface 15 corresponding to the lifting surface 11 of the lifting block 12. The opening support rod 7, the lifting block 12 and the lifting matching block 14 arranged in the accommodating cavity 13 of the handle 1 form the lifting component. Further referring to FIGS. 6, 13 and 15, the moving mandrel 5 drives the opening support rod 7 to move, and the lifting block 12 on the side of the opening support rod 7 cooperates with the lifting matching block 14 in the accommodating cavity 13 through the contact between the tilted lifting surface 11 and the lifting matching surface 15, so that the opening support rod 7 moves up and down to drive the opening plates 6 to vertically open, thereby completing the vertical opening operation of the processing device.

Figure 5:
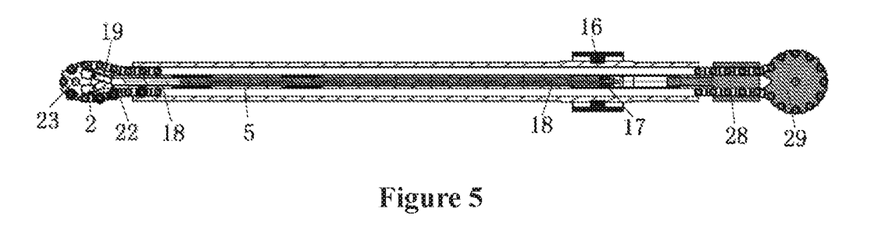
FIG. 5 is a schematic sectional view of FIG. 3.
Figure 12:
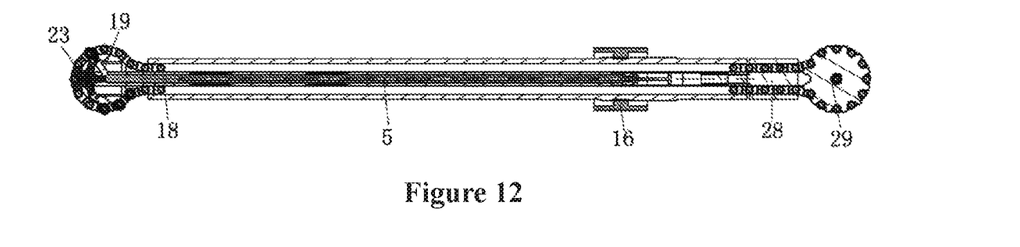
FIG. 12 is a schematic sectional view of FIG. 10.

Referring to FIGS. 5 and 12, the horizontal expansion mechanism further includes a handheld rotating member 16, a connector 17 and a moving rod 18. The moving rod 18 is connected to block bodies of the arc-shaped expansion blocks 2 through multiple connecting rods 19. The handheld rotating member 16 is sleeved on the handle body at the control end of the handle 1 and is screwed with the handle body. Another scale is carved at the handle body, which can clearly show the horizontal expansion of the processing device and is also convenient for medical staff to adjust in real time. The connector 17 is fixed in the handheld rotating member 16, and the handheld rotating member is connected with the moving rod 18 through this connector 17. The handheld rotating member 16 rotates and moves on the handle body of the handle, thereby driving the moving rod 18 to move along the axial direction of the handle through the connector 17. The moving rod 18 moves and horizontally pushes the arc-shaped expansion blocks 2 to expand through the connecting rod 19. Therefore, the transmission member is horizontally expanded, so that the processing portion 3 horizontally moves out from the vertical space of the opening members and contacts with the bone surface of the vertebral body, thereby completing the horizontal expansion operation of the processing device.

Figure 7:
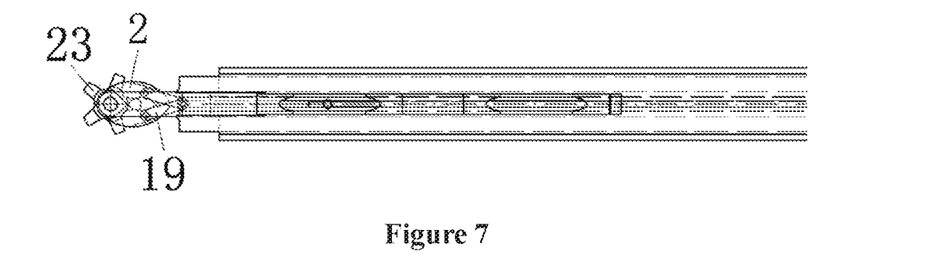
FIG. 7 is a schematic structural view of a portion of a horizontal expansion mechanism in FIG. 5 located at the processing end of the handle.
Figure 14:
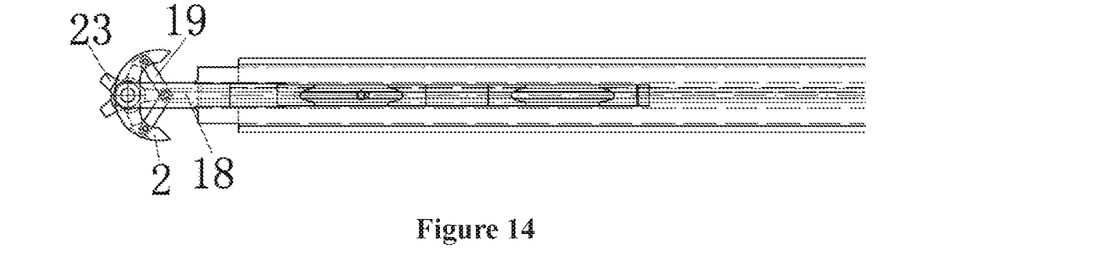
FIG. 14 is a schematic structural view of the portion of the horizontal expansion mechanism in FIG. 10 located at the processing end of the handle.

Referring to FIGS. 7, 14 and 16, a pair of fixing accessories 20 arranged symmetrically up and down extend horizontally at the processing end of the handle 1, the fixing accessories 20 are located in the vertical space of the expansion members, and are provided with through holes 21. End portions of the pair of arc-shaped expansion blocks 2 are connected with the through holes 21 of the fixing accessories 20 through a pin shaft and serve as horizontal expansion support ends, and cooperate with the moving rod 18 and the connecting rod 19 to realize the horizontal expansion of the arc-shaped expansion blocks 2.

In order to improve the transmission efficiency, the transmission member is selected as a transmission chain 22, the transmission chain 22 is in contact with the arc-shaped outer surface of the arc-shaped expansion block 2, and a first chain wheel 23 engaged with the transmission chain 22 is coaxially provided at the horizontal expansion support end.

Figure 18:
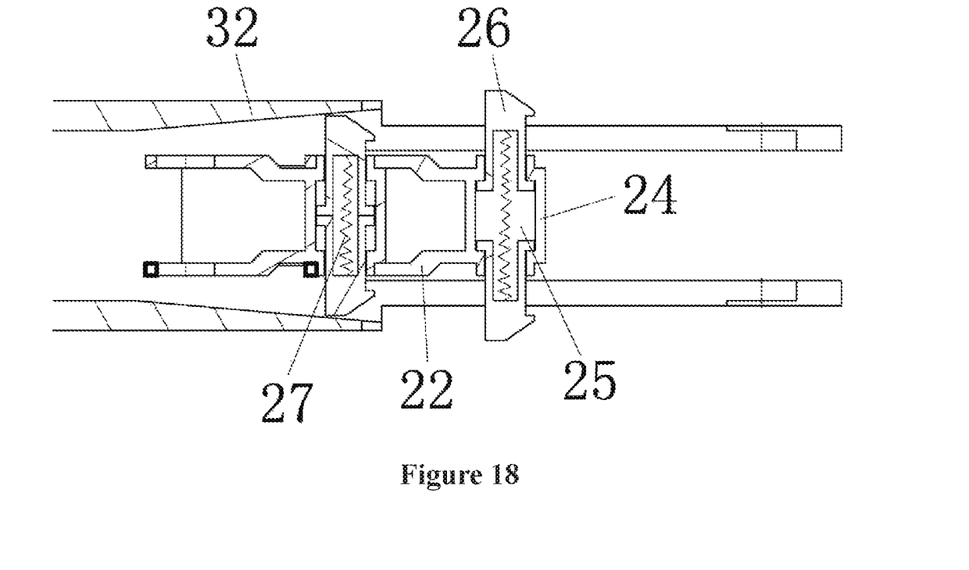
FIG. 18 is a schematic structural view of a processing unit and a guiding structure.

Referring to FIG. 18, the processing portion 3 includes multiple processing units. Each of the processing units includes a sleeve 24 and processing knifes 26 symmetrically arranged at two ends of the sleeve 24. The sleeve 24 is vertically embedded and fixed to the transmission chain 22. A moving space 25 is provided in the sleeve 24. A knife head of the processing knife 26 protrudes from the sleeve 24, and a knife handle of the processing knife 26 is provided in the moving space 25 of the sleeve 24. An elastic member 27 is connected between the processing knifes 26. When the processing device is in the non-working state, the vertical opening mechanism maintains the contracted state. The opening member acts on the knife head of the processing knife 26, so that the elastic member 27 is compressed under force. The knife handle of the processing knife 26 moves along the axial direction of the sleeve 24 in the moving space 25 of the sleeve 24, so that the processing portion 3 is accommodated in the vertical space of the opening members, referring to FIGS. 1 to 3 for the specific state. When the processing device is in the working state, the processing portion 3 horizontally moves out from the vertical space of the opening members. The knife handle of the processing knife 26 moves along the axial direction of the sleeve 24 in the moving space 25 under the elastic force of the elastic member 27 until the knife head of the processing knife 26 contacts with the bone surface of the vertebral body, referring to FIGS. 8 to 10 for the specific state. Besides, the elastic member 27 functions to keep an abutting state between the processing knife 26 and the bone surface of the vertebral body after the intervertebral space is expanded, and to process the irregular intervertebral space.

Referring to FIGS. 3 and 10, the control portion 4 includes a movement control block 28 and a manual chain wheel 29. A handle connector 30 and a chain wheel connector 31 extend horizontally on two sides of the movement control block 28, respectively. The handle connector 30 is movably connected with the control end of the handle 1 by means of insertion. The chain wheel connector 31 is pivotally connected to an axis of the manual chain wheel 29. The transmission chain 22 is connected to the first chain wheel 23 and the manual chain wheel 29, and a transmission space (not shown in the figure) for the transmission chain 22 is provided in the handle 1 and the movement control block 28. When the processing device is in the working state, the arc-shaped expansion blocks 2 of the horizontal expansion mechanism drive the transmission chain 22 to expand, and the transmission chain 22 is engaged with the manual chain wheel 29, so that the movement control block 28 and the manual chain wheel 29 move along the axial direction of the handle 1 towards the processing end of the handle 1. The manual chain wheel 29 is operated to rotate the transmission chain 22, so that multiple processing units contact with the bone surface of the vertebral body, thereby completing the processing operation of the processing device on the bone surface of the vertebral body.

Besides, tilted guiding structures 32 are provided at two ends of the transmission space of the transmission chain 22 where the handle 1 and the movement control block 28 are located, as shown in FIG. 18. The provision of the guiding structure 32 can more advantageously guide the processing portion 3 to move the with the transmission chain 22 into the transmission space inside the handle 1 and the movement control block 28.

The specific operation principle of the processing devices is described as follows.

The processing device is inserted between two vertebral bodies, so that the opening plates 6 which are symmetrically arranged up and down are in contact with the bone surfaces of the two vertebral bodies.

According to actual operation needs, the medical staff determines the pulling distance of the handheld control component 9, and then slowly pulls the handheld control component 9 to a specified position along the scale at the side wall of the long strip-shaped through hole 10 while observing the real-time pressure data sent back by the pressure sensor on the surface of the opening plate 6. The movement of the handheld control component 9 drives the moving mandrel 5 to move along the axial direction of the handle 1, thereby broadening the two vertebral bodies into a specified height by driving the opening support rod 7 to move and cooperate with the lifting component. Since the handheld control component 9 is in interference fit with the side wall of the long strip-shaped through hole 10, the handheld control component 9 can still keep the position unchanged after being released, thereby keeping the opening height unchanged.

According to the requirement of the processing area of the bone surface of the vertebral body, the medical staff determines the maximum radian of the processing portion 3 for the processing of the bone surface of the vertebral body, so as to determine the expansion degree of the horizontal expansion mechanism. And then, the medical staff manually rotates the handheld rotating member 16, and rotates the handheld rotating member 16 to the specified scale according to the scale at the handle body. The rotation of the handheld rotating member 16 drives the moving rod 18 to move in the handle 1 along the axial direction of the handle 1 through the connector 17. The moving rod 18 is connected with the arc-shaped expansion block 2 through the connecting rod 19, and the fixing accessory 20 is pivotally connected to the end portion of the arc-shaped expansion block 2 to serve as the horizontal expansion support end, and then the arc-shaped expansion block 2 is opened through the connecting rod 19 to expand to the specified radian while moving the moving rod 18. Since the handheld rotating member 16 is screwed with the handle 1, after the handheld rotating member 16 is rotated to the specified position, the handheld rotating member 16 can also keep the position unchanged after being loosened.

While the arc-shaped expansion block 2 expands, the transmission chain 22 in contact with the outer arc surface of the arc-shaped expansion block 2 also expands synchronously. After losing the pressing force of the upper and lower opening plates 6, the processing knifes 26 of the processing portion 3 vertically arranged on the transmission chain 22 move to the two ends of the sleeve 24 in the moving space 25 of the sleeve 24 under the action of the elastic force of the elastic member 27 connected between the processing knifes 26, so that the processing knifes 26 are in contact with the bone surfaces of the two vertebral bodies respectively, and remain in the abutting state under the action of the elastic member 27.

In the meantime, the manual chain wheel 29 at the control end of the handle 1 and the movement control block 28 move along the direction from the control end of the handle 1 to the processing end by a certain distance due to the horizontal expansion of the transmission chain 22 at the processing end of the handle 1, and then remain stable. The medical staff manually rotates the manual chain wheel 29, so that the transmission chain 22 engaged with the manual chain wheel 29 moves, thereby driving the multiple processing knifes 26 on the transmission chain 22 to contact with the bone surface of the vertebral body to realize the processing operation. After the processing operation of an arc on the bone surface of the vertebral body is finished, the horizontal expansion mechanism is repeatedly operated to adjust the expansion radian thereof, so that the processing arc of the processing knifes 26 on the bone surface of the vertebral body is changed until the processing operation of the bone surface of the whole vertebral body is completed.

After the processing operation is finished, the operation of the manual chain wheel 9 is stopped, the handheld rotating member 16 is adjusted to drive the arc-shaped expansion block 2 to retract, and then the handheld control member 9 is pulled to reduce the opening height of the opening plates 6, and the multiple processing units on the transmission chain 22 are compressed and accommodated in the vertical space between the opening plates 6, and then the whole processing device is taken out from between the two vertebral bodies, thereby completing the processing operation of the whole vertebral body endplate.

Based on the above description of the disclosed embodiments, those skilled in the art are capable of carrying out or using the present application. Many changes to these embodiments are obvious to those skilled in the art, and general principles defined herein may be implemented in other embodiments without departing from the spirit or scope of the present application. Hence, the present application is not limited to the embodiments disclosed herein, but is to conform to the widest scope in accordance with the principles and novel features disclosed herein.

The invention claimed is:

1. A vertebral body endplate processing device, comprising
 a handle,
 a vertical opening mechanism,
 a horizontal expansion mechanism,
 and a processing mechanism,
 wherein two ends of the handle respectively are a processing end and a control end, the vertical opening mechanism comprises a pair of opening members that are symmetrically arranged up and down and arranged at the processing end of the handle, the horizontal expansion mechanism comprises a pair of arc-shaped expansion blocks arranged horizontally and a transmission member in contact with an outer side surface of the arc-shaped expansion blocks, the processing mechanism comprises a processing portion vertically arranged on the transmission member and a control portion connected with the transmission member, the arc-shaped expansion blocks and the processing portion are arranged at the processing end of the handle, and the control portion is arranged at the control end of the handle;

when the processing device is in a non-working state, the vertical opening mechanism and the horizontal expansion mechanism maintain a contracted state, and the processing portion is located within a vertical space between the opening members; when the processing device is in a working state, the opening members of the vertical opening mechanism are in contact with a bone surface of the vertebral body and are vertically opened; the arc-shaped expansion blocks of the horizontal expansion mechanism is configured to drive the transmission member to horizontally expand, the processing portion is configured to horizontally move out from the vertical space of the opening members and to contact with the bone surface of the vertebral body, and the control portion is configured to control the transmission member to move, so as to drive the processing portion to process the bone surface of the vertebral body.

2. The vertebral body endplate processing device according to claim 1, wherein the vertical opening mechanism further comprises a moving mandrel provided inside the handle and configured to move along an axial direction of the handle, an end of the moving mandrel is connected with the opening members vertically arranged and located at the processing end of the handle, a lifting component configured to cause the opening members to move up and down is provided at the processing end of the handle, and the moving mandrel is configured to drive the opening members to move and cooperate with the lifting component to vertically broaden the opening members to a same height as the handle.

3. The vertebral body endplate processing device according to claim 2, wherein the opening members comprises an opening plate with a pressure sensor on a surface of the opening plate, an opening support rod extends at an end portion of the opening plate, a fixing hole is provided on a surface of the opening support rod, an end of the moving mandrel is of a T-shaped structure and penetrates through the fixing hole on the surface of the opening support rod and is fixed thereto, and another end of the moving mandrel is connected with a handheld control component, a long strip-shaped through hole is provided in a handle body at the control end of the handle, the handheld control component is arranged in the long strip-shaped through hole and is in interference fit with two side walls of the long strip-shaped through hole, and the handheld control component is configured to move in the strip-shaped through hole and drive the moving mandrel to move inside the handle.

4. The vertebral body endplate processing device according to claim 3, wherein a plurality of lifting blocks with a tilted lifting surface vertically extend downward on a side of the opening support rod, an accommodating cavity for accommodating the opening support rod is provided at the handle body of the processing end of the handle, a lifting matching block corresponding to the lifting blocks of the opening support rod is provided in the accommodating cavity, the lifting matching block is provided with a tilted lifting matching surface corresponding to the lifting surface of the lifting blocks, the opening support rod, the lifting blocks and the lifting matching block arranged in the accommodating cavity of the handle form the lifting component, the moving mandrel is configured to drive the opening support rod to move, and the lifting blocks on the side of the opening support rod are configured to cooperate with the lifting matching block in the accommodating cavity through the contact between the tilted lifting surface and the lifting matching surface, and the opening support rod is moved up and down to drive the opening plates to vertically open to complete the vertical opening operation of the processing device.

5. The vertebral body endplate processing device according to claim 1, wherein the horizontal expansion mechanism further comprises a handheld rotating member, a connector and a moving rod, the moving rod is connected to block bodies of the arc-shaped expansion blocks through a plurality of connecting rods, the handheld rotating member is sleeved on a handle body at the control end of the handle and is screwed with the handle body, the connector is fixed in the handheld rotating member, and the handheld rotating member is connected with the moving rod through the connector, the handheld rotating member is configured to rotate and move on the handle body of the handle to drive the moving rod to move along an axial direction of the handle through the connector, the moving rod is configured to move and horizontally push the arc-shaped expansion blocks to expand through the connecting rods, the transmission member is horizontally expanded, and the processing portion is horizontally is moved out from the vertical space of the opening members and contacts with the bone surface of the vertebral body to complete the horizontal expansion operation of the processing device.

6. The vertebral body endplate processing device according to claim 5, wherein a pair of fixing accessories arranged symmetrically up and down extend horizontally at the processing end of the handle, the fixing accessories are located in the vertical space of the expansion members, and are provided with through holes; and end portions of the pair of arc-shaped expansion blocks are connected with the through holes of the fixing accessories through a pin shaft and serve as horizontal expansion support end, and cooperate with the moving rod and the connecting rods to realize the horizontal expansion of the arc-shaped expansion blocks.

7. The vertebral body endplate processing device according to claim 6, wherein the transmission member is a transmission chain, the transmission chain is in contact with the outer side surface of the arc-shaped expansion blocks, and a first chain wheel engaged with the transmission chain is coaxially provided at the horizontal expansion support end.

8. The vertebral body endplate processing device according to claim 7, wherein the processing portion comprises a plurality of processing units, each of the processing units comprises a sleeve and processing knives symmetrically arranged at two ends of the sleeve, the sleeve is vertically embedded and fixed to the transmission chain, a moving space is provided in the sleeve, a knife head of the processing knives protrudes from the sleeve, knives handles of the processing knives are provided in the moving space of the sleeve, and an elastic member is connected between the processing knives, when the processing device is in the non-working state, the vertical opening mechanism maintains the contracted state, the opening members act on the knives heads of the processing knives acts on, and the elastic member is compressed under force, knives handles of the processing knives move along an axial direction of the sleeve in the moving space of the sleeve, and the processing portion is accommodated in the vertical space of the opening members; and when the processing device is in the working state, the processing portion horizontally moves out from the vertical space of the opening members, the knives handles of the processing knives move along the axial direction of the sleeve in the moving space under the elastic force of the elastic member until the knives heads of the processing knives contact with the bone surface of the vertebral body.

9. The vertebral body endplate processing device according to claim 8, wherein the control portion comprises a movement control block and a manual chain wheel, a handle connector and a chain wheel connector extend horizontally on two sides of the movement control block, respectively, and the handle connector is movably connected with the control end of the handle by means of insertion, the chain wheel connector is pivotally connected to an axis of the manual chain wheel, the transmission chain is connected to the first chain wheel and the manual chain wheel, and a transmission space for the transmission chain is provided in the handle and the movement control block, when the processing device is in the working state, the arc-shaped expansion blocks of the horizontal expansion mechanism drive the transmission chain to expand, the transmission chain is engaged with the manual chain wheel, and the movement control block and the manual chain wheel move along the axial direction of the handle towards the processing end of the handle, the manual chain wheel is operated to rotate the transmission chain, and the plurality of processing units contact with the bone surface of the vertebral body, thereby completing the processing operation of the processing device on the bone surface of the vertebral body.

10. The vertebral body endplate processing device according to claim 9, wherein tilted guiding structures are provided at two ends of the transmission space of the transmission chain where the handle and the movement control block are located.

* * * * *